(12) United States Patent
Liebing

(10) Patent No.: US 10,835,653 B2
(45) Date of Patent: Nov. 17, 2020

(54) FLUID PUMP CHANGEABLE IN DIAMETER, IN PARTICULAR FOR MEDICAL APPLICATION

(71) Applicant: ECP ENTWICKLUNGSGESELLSCHAFT MBH, Berlin (DE)

(72) Inventor: Reiner Liebing, Berlin (DE)

(73) Assignee: ECP ENTWICKLUNGSESELLSCHAFT MBH, Aachen (DE)

( * ) Notice: Subject to any disclaimer, the term of this patent is extended or adjusted under 35 U.S.C. 154(b) by 36 days.

(21) Appl. No.: 16/369,503

(22) Filed: Mar. 29, 2019

(65) Prior Publication Data

US 2019/0224391 A1 Jul. 25, 2019

Related U.S. Application Data

(63) Continuation of application No. 16/293,956, filed on Mar. 6, 2019, which is a continuation of application
(Continued)

(30) Foreign Application Priority Data

May 5, 2009 (EP) .................................... 09075221

(51) Int. Cl.
*A61M 1/10* (2006.01)
*A61M 1/12* (2006.01)
(Continued)

(52) U.S. Cl.
CPC .......... *A61M 1/1024* (2014.02); *A61M 1/101* (2013.01); *A61M 1/1013* (2014.02); *A61M 1/1034* (2014.02); *A61M 1/122* (2014.02); *F04C 2/02* (2013.01); *F04C 14/22* (2013.01); *F04D 29/043* (2013.01); *F04D 29/046* (2013.01);
(Continued)

(58) Field of Classification Search
CPC .. A61M 1/101; A61M 1/1013; A61M 1/1024; A61M 1/1031; A61M 1/1032; A61M 1/1034; A61M 1/1036; A61M 1/122; A61M 1/125; F04D 29/043;
(Continued)

(56) References Cited

U.S. PATENT DOCUMENTS

| 7,022,100 | B1 * | 4/2006 | Aboul-Hosn | ......... | A61M 1/125 604/6.11 |
| 7,491,163 | B2 * | 2/2009 | Viole | .................. | A61M 1/3653 600/16 |

(Continued)

*Primary Examiner* — Igor Kershteyn
(74) *Attorney, Agent, or Firm* — Botos Churchill IP Law LLP

(57) ABSTRACT

A fluid pump device changeable in diameter is provided. The device has a pump housing which is changeable in diameter and with a rotor which is changeable in diameter. The device has at least one delivery element for fluid, as well as a drive shaft on which the rotor is rotatably mounted. A bearing arrangement is arranged on the drive shaft or its extension, at the distal end of the drive shaft behind the rotor seen from the proximal end of the drive shaft. The bearing arrangement has struts, which elastically brace between a hub of the bearing arrangement and the pump housing.

16 Claims, 5 Drawing Sheets

Related U.S. Application Data

No. 15/281,796, filed on Sep. 30, 2016, now Pat. No. 10,265,448, which is a continuation of application No. 14/576,396, filed on Dec. 19, 2014, now Pat. No. 9,512,839, which is a continuation of application No. 13/318,678, filed as application No. PCT/EP2010/002827 on Apr. 29, 2010, now Pat. No. 8,944,748.

(60) Provisional application No. 61/175,519, filed on May 5, 2009.

(51) Int. Cl.
  *F04D 29/043* (2006.01)
  *F04D 29/046* (2006.01)
  *F04D 29/18* (2006.01)
  *F04D 29/24* (2006.01)
  *F04D 29/52* (2006.01)
  *F04C 2/02* (2006.01)
  *F04C 14/22* (2006.01)

(52) U.S. Cl.
  CPC ......... *F04D 29/181* (2013.01); *F04D 29/242* (2013.01); *F04D 29/528* (2013.01); *A61M 1/1031* (2014.02); *A61M 1/1032* (2014.02); *A61M 1/1036* (2014.02); *A61M 1/125* (2014.02); *Y10S 415/90* (2013.01)

(58) Field of Classification Search
  CPC .... F04D 29/046; F04D 29/181; F04D 29/242; F04D 29/528; F04C 2/02; F04C 14/22; Y10S 415/90
  See application file for complete search history.

(56) References Cited

U.S. PATENT DOCUMENTS

| | | | | |
|---|---|---|---|---|
| 2002/0169413 | A1* | 11/2002 | Keren | A61M 1/3659 604/101.03 |
| 2003/0135086 | A1* | 7/2003 | Khaw | A61M 1/1024 600/16 |
| 2008/0103591 | A1* | 5/2008 | Siess | A61M 1/101 623/3.13 |
| 2009/0093764 | A1* | 4/2009 | Pfeffer | A61M 1/1015 604/151 |
| 2009/0093796 | A1* | 4/2009 | Pfeffer | A61M 1/12 604/530 |
| 2009/0171137 | A1* | 7/2009 | Farnan | A61M 1/101 600/16 |

* cited by examiner

FLUID PUMP CHANGEABLE IN DIAMETER, IN PARTICULAR FOR MEDICAL APPLICATION

CROSS-REFERENCE TO RELATED APPLICATIONS

This application is a continuation application of pending U.S. patent application Ser. No. 16/293,956, filed Mar. 6, 2019, which is a continuation application U.S. patent application Ser. No. 15/281,796, filed Sep. 30, 2016 (now allowed), which is a continuation application of U.S. patent application Ser. No. 14/576,396, filed Dec. 19, 2014 (now U.S. Pat. No. 9,512,839), which is a continuation application of U.S. patent application Ser. No. 13/318,678, filed Nov. 29, 2011 (now U.S. Pat. No. 8,944,748), which is a 371 national stage filing of PCT International Application No. PCT/EP2010/002827, filed Apr. 29, 2010, which claims the benefit of U.S. Provisional Application No. 61/175,519, filed May 5, 2009, and European Patent Application 09075221.3, filed May 5, 2009, all of which are hereby incorporated by reference in their entireties. International Application No. PCT/EP2010/002827 was published under PCT Article 21(2) in English.

BACKGROUND OF THE INVENTION

The invention lies in the field of mechanics, in particular precision mechanics, and may be advantageously applied to the medical field.

However, independently of the application in the medial sector, applications in other fields may be envisaged, where a fluid pump is to be operated under restricted spatial conditions or at poorly accessible locations.

This is particularly the case with minimal-invasive medical technology, where often medical instruments or apparatus must be brought to the location of application, for example through blood vessels, with an as gentle as possible treatment of the patient. It is particularly in this context that the application of blood pumps in combination with catheters has become known, which for example may be introduced into a heart chamber whilst supporting the heart pumping activity.

Since a certain size is necessary for an optimised performance of such a pump, which however is limited by the diameter of the large blood vessels of the body which end in the heart, it is already known to use fluid pumps which are changeable in their radius for this purpose, which may be expanded after introduction into the heart chamber.

BRIEF SUMMARY OF THE INVENTION

This is made possible either by way of special mechanisms, which permit an actuation of a spanning mechanism of the pump by way of a catheter, as is known for example from the US patent document US 2008/0103591 or WO 03/103745, or by way of the use of so-called memory materials, which may assume different shapes when changing the temperature of the surroundings, and may be brought into the desired end shape by way of temperature change.

An alternative solution is known from U.S. Pat. No. 7,393,181 B2, with which flexible rotor blades may be applied onto a hub and be reversibly deformable in a manner such that they are automatically set up on pump operation.

However, tight limits are placed on the expansion ability of such pumps due to the necessity of accommodating a drive shaft as well as a rotor and pump housing within a small diameter.

In this context, it is the object of the present invention to create a fluid pump, which with as little as possible design effort, permits an as simple and as large as possible changeability of the diameter.

According to the invention, this object is achieved by the features of patent claim 1.

Thereby, a pump housing which is changeable in diameter as well as, as the case may be, also a rotor changeable in diameter, is provided with at least one delivery element for the fluid, as well as an actuation means, in particular a pull means, at whose end which is distal seen from the introduction location of the catheter, the fluid pump is arranged.

The actuation means is displaceable in a longitudinal direction. The pump housing and the rotor are displaceable relative to one another to such an extent in the longitudinal direction of the actuation means by way of the actuation means, that they may be arranged behind one another in the longitudinal direction, or with a mutual overlapping in the longitudinal direction, which is smaller than the overlapping during the operation of the fluid pump, in order to permit an efficient compression to a smaller diameter. This may be realised by way of either the pump housing or the rotor or both being displaceable with respect to the actuation means. In this context, the pump housing is to be understood as that in which the rotor is located and rotates, preferably without wall contact, during pump operation.

Thus the rotor may be moved at least partly out of the pump housing for an efficient compression of the rotor. The compression movement of the pump housing is then not limited by the rotor, which is completely accommodated in it.

One may also envisage the actuation means between the distal end and the proximal end at least in sections running in a sleeve or parallel to a sleeve. It is however also possible for the actuation means to run parallel to another guide means, for example a guide wire, and for no sleeve to be provided.

The actuation means may for example be used as a pull means and be designed as a drive shaft, at whose proximal end a rotation drive for the pump is provided. The drive shaft in this case is rotatable and furthermore displaceable in the longitudinal direction.

Apart from this embodiment, there is also the possibility of driving the pump by way of an implantable miniature motor which is arranged at the distal end of a sleeve or another guide means, and which is implantable into the body, or also a hydraulic microturbine. Instead of the drive shaft, the fluid pump then has its own actuation means, such as for example a cable or a wire or likewise, which displaces the rotor or other parts of the pump, in particular also pulls a bearing arrangement into the pump housing.

Furthermore, in the first mentioned case, there is also the possibility of applying a more suitable pull means additionally to a drive shaft. This permits the drive shaft to be optimised with regard to the demands concerning the torque transmission and running time, and permits the pull means to be optimised independently of this, with regard to the pulling function.

Such a pull means may for example be a cable of plastic or a wire cable or also a wire or any other suitable pull means. In the case of the use of an implantable miniature electric motor, one could for example also use the cable necessary for operation of the motor, as a pull means, and in the case of the use of a hydraulic microturbine, the hydraulic conduits or flexible tubing required for the operation of this turbine may also be used as pull means.

If the actuation means is stiff enough, for example is designed as wire, then a push movement may also be designed in a controlled manner. With this for example, the pump housing may also be pushed to the rotor in the longitudinal direction of the actuation means.

The pump housing may for example consist of an elastic framework, e.g. of a memory alloy or of a plastic, which is coated with a membrane, for example of polyurethane. The pump housing on the other hand may however also consist of segments which are moveable to one another, such as e.g. scales or lamellae which as a whole are movable and may be compressed, wherein individual scales/segments or lamellae may be stiff per se or flexible. The rotor, as the case may be, is compressible per se by way of the fact that either individual delivery elements of the rotor may be folded or pivoted onto the shaft for reducing the diameter, or the fact that the rotor consists of a membrane which may be stretched out by way of one or more tautening elements.

Additionally to the outlined embodiments of the pump housing and the rotor, also other compressible and expandable construction shapes are conceivable for the application of the invention.

It is advantageous for a particularly good compressibility of the arrangement, if the pump housing and the rotor are displaceable to one another so far in the longitudinal direction of the actuation means, that they may be arranged behind one another in the longitudinal direction, or with a mutual overlapping in the longitudinal direction, which is smaller than the overlapping during the operation of the fluid pump. The different parts thereby may be displaceable on a drive shaft, which either forms the actuation means or whose extension is in the region of the pump, if an implantable miniature motor is provided at the end of the sleeve.

A particularly advantageous embodiment of the invention envisages a bearing arrangement being arranged on the actuation means or its extension, at the distal end of the actuation means or its extension, behind the rotor seen from the rotation drive.

One achieves a particularly quiet and smooth running of the rotor by way of a further mounting at the distal end of the pump housing being provided additionally to a mounting at the proximal end of the pump housing. The respective bearing arrangement may likewise be movable relative to the pump housing within the framework of the invention. It is advantageously displaceable on the actuation means or its extension, in their longitudinal directions, or at least displaceable with the actuation means or the extension, with respect to the rotor and the pump housing, as long as the actuation means itself is displaceable in the longitudinal direction.

After the expansion of the fluid pump device, the bearing arrangement may be brought by way of this to its location of application at the distal end of the pump housing, by way of a further displacement movement.

A further advantageous design of the invention envisages the bearing arrangement being displaceable relative to the rotor in the longitudinal direction of the actuation means.

With this, the bearing arrangement as well as the rotor may be compressed and expanded independently of one another and be displaced to one another in the longitudinal direction only after the attachment of the fluid pump device, in order to achieve the operating arrangement.

If the bearing arrangement is axially displaceable to the actuation means or the extension, then an abutment body should be provided on these, for example at their end which on pulling back the actuation means, entrains the bearing arrangement in the direction of the activation device.

The bearing arrangement for its part may then abut against the rotor and also move this in the direction of the pump housing up to the end position.

One may also envisage the bearing arrangement being movable with the rotor into the inside of the pump housing, and struts arranged in a star-like manner being provided, which elastically brace between a hub of the beating arrangement and the pump housing.

This may advantageously be achieved by way of the struts being elastically pivotably fastened on the hub of the bearing arrangement.

For this purpose, the struts just as the bearing arrangement, may for example consist of an elastic plastic or rubber, or of a spring-elastic metal.

It may also be advantageous for the struts to be radially extended by way of folding open in the course of the movement of the drive shaft, by way of axial compression of the bearing arrangement. This e.g. is possible if the bearing arrangement comprises two rings which are mutually to one another in the axial direction, between which the struts are fastened, wherein the struts bear in a flat manner given a larger distance of the rings, and are expanded in a bead-like manner with a pushing-together of the rings.

The struts in the braced condition may advantageously form an inflow cage at the distal end of the fluid pump, which on the one hand prevents the rotor from coming into contact with body tissue and one the other hand ensures that any larger coagulated masses, which are located in the fluid to be delivered, may not penetrate into the pump housing.

Moreover, it is advantageous to design the actuation means in a displaceable manner with respect to the sleeve in the longitudinal direction, in particular to the rotation drive at the proximal end of the sleeve, in order to effect the different axial displacement movements of the pump housing, the rotor and the bearing arrangement to one another.

The sleeve thereby is usually designed as a catheter in the field of the medical application. Such a catheter although being flexible, is also so stiff that it may be pushed through a blood vessel. The catheter is usually connected to the pump housing in a fluid-tight manner, wherein the actuation means, for example a drive shaft, is introduced in an as sealed as possible manner into the pump housing through a rotation lead-through.

The catheter, at the proximal end which usually lies outside the body of the patient, is connected in a fluid-tight manner to an actuation device and for example also to an electromotoric drive, inasmuch as no implanted micromotor is preferred in the region of the fluid pump.

Advantageously, the catheter is filled with a body-compatible fluid, for example a saline solution, in order on the one hand to prevent the penetration of gas bubbles into the body and on the other hand, as the case may be to lubricate and cool the shaft which usually rotates at 20,000-35,000 revolutions per minute.

The present invention in the case that it is provided within the sleeve of a drive shaft, may further advantageously be designed such that the drive-side end of the drive shaft is connected to a drive body which is arranged in a sealed housing and which may be driven in a magnetic and rotatory manner from outside the housing.

This embodiment permits the drive of the drive shaft through a magnetically inactive housing, without a rotation lead-through which is to be sealed off, by way of a rotation field being applied, which sets the drive body located in the housing and thus the drive shaft, into rotation.

A displacement ability of the drive shaft in the longitudinal direction according to the invention is achieved by way of the drive body being displaceable in the longitudinal direction of the drive shaft, and being driven on the cover side by way of a changing magnetic field.

Due to the cover-side transmission of the drive forces, this is independent of an axial displacement of the drive body on pulling or pushing the shaft.

However, one may also envisage the drive shaft being connected in a fixed manner to a catch body, which for its part is displaceably guided in a direct manner in the rotor in the longitudinal direction of the drive shaft.

In this case, the drive body is arranged in a stationary manner in the axial direction of the drive shaft, and only a catch body which is connected to the rotor in a rotationally fixed manner, for its part is axially displaceable with the drive shaft. Such a catch body may for example be designed as a body which is polygonal in cross section, for example an octagonal body.

The invention apart from a fluid pump device of the initially mentioned type, also relates to a method for operation of such a device, wherein one envisages the fluid pump device in the compressed condition being brought to a location of application, thereafter at least partly expanding the pump housing and thereafter displacing the pump housing and the rotor to one another in the longitudinal direction of the actuations means, in particular of a drive shaft of the rotor, such that the rotor is completely accommodated in the pump housing.

A greater compression of the individual parts by way of their staggering in the longitudinal direction of the actuation means is possible with the mentioned method steps, specifically by way of firstly the individual elements of the pump housing, the rotor and the bearing arrangement being brought to the application location, thereafter at least partly expanded and only after this being brought into the constellation necessary for operation by way of relative axial displacement.

After the introduction of the arrangement for example into the body of a patient, with the means of the invention, one may for example retract the drive shaft, and thus the bearing arrangement as well as the rotor may be moved in the direction of the pump housing, until the rotor is located completely in the pump housing and is supported by the bearing arrangement as the case may be.

As to whether the rotor is expanded before or after it is introduced into the pump housing is neither here nor there, just as is the case with the possibility of only partly expanding the pump housing as much as is necessary firstly before the introduction of the rotor, in order to introduce the rotor, or whether the pump housing is completely expanded already before the introduction of the rotor.

BRIEF DESCRIPTION OF THE DRAWINGS

The invention is hereinafter shown and described hereinafter by way of one embodiment example in a drawing. Thereby, there are shown in.

DETAILED DESCRIPTION OF THE INVENTION

Figure 1:
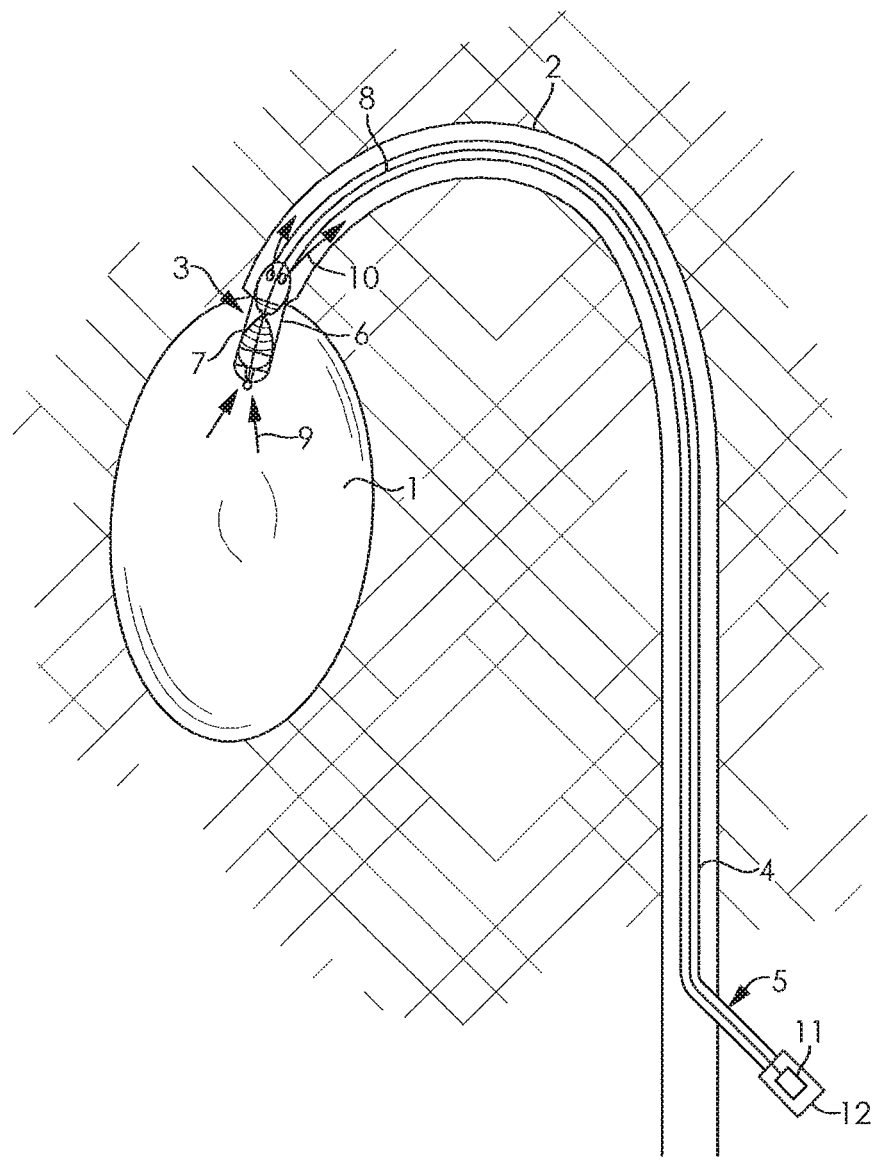
FIG. 1 a schematic overview of a fluid pump device, wherein the pump is inserted into a heart chamber, FIG. 2 a three-dimensional picture of a pump rotor, FIG. 3. a lateral view of the pump housing, of the rotor and of a bearing arrangement, FIG. 4. a lateral view of the pump housing with a rotor located therein, FIG. 5. a detail of the pump housing in a three-dimensional representation, FIG. 6. a bearing arrangement of FIG. 6 in a front view, FIG. 7. the bearing arrangement of FIG. 6 in a front view, FIG. 8. a further bearing arrangement, FIG. 9. a bearing arrangement as from FIG. 8, in a compressed condition, FIG. 10. a further bearing arrangement in a lateral view, FIG. 11. the proximal end of a drive shaft with a coupling to a rotation drive, FIG. 12 another design of the proximal shaft end, with another coupling to a drive, FIG. 13. an arrangement without a bearing at the distal end of the rotor, in the condition staggered in the longitudinal direction, FIG. 14. the arrangement of FIG. 13, in the operating condition, and FIG. 15. a further development of the arrangement according to FIGS. 13 and 14.

FIG. 1 shows a heart chamber, which is connected to a blood vessel 2, into which blood is to be pumped. For supporting the pump activity, a fluid pump 3 is introduced into the heart chamber 1, which there sucks blood and pumps this into the blood vessel 2.

A catheter 4 is introduced through a lock 5 into the blood vessel 2, through which lock the catheter may also be pulled out again. The catheter 4 at its distal end carries the pump 3 in the form of a pump housing 6 connected to the catheter, and a rotor 7. The rotor 7 is rotatably mounted on a drive shaft 8 and comprises delivery elements, which on rotation suck the blood in the direction of the arrows 9 or eject it in the direction of the arrows 10 into the blood vessel 2. For this, the delivery elements in the shown representation, which shows the explained position of the fluid pump, have a helically arranged delivery blade surface.

The construction of the pump housing and the rotor will be dealt with in more detail further below.

The drive shaft 8 runs within the catheter, which forms a sleeve in the context of the invention and is driven by the drive 11, which is accommodated in a housing 12. The drive shaft thereby may form an actuation means. The drive elements are only schematically shown in FIG. 1 and are explained further below likewise, in a more detailed manner.

Figure 2:
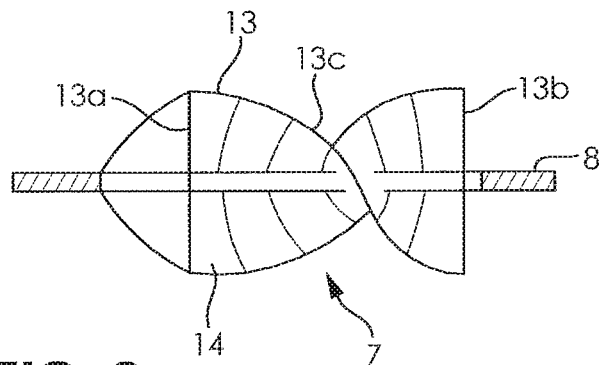

FIG. 2 in detail shows a pump motor with two helical delivery blades 13, 14, which are offset to one another by 180° on the periphery of the drive shaft 8. The individual delivery blades consist of spanning elements such as for example struts 13a, 13b, as well as a frame 13c which is tautened with a membrane, for example of polyurethane or polyethylene. The frame and the struts may for example consist of a memory material which assumes its shape dependent on temperature. Then in a compressed form at a first temperature, preferably cooled, such a pump rotor may be introduced into the body of the patient and there may automatically unfold or expand after heating to the body temperature or subsequent further heating.

However, it is also conceivable to automatically erect the pump rotor by way of a rotation drive in the operation direction, by way of the fluid to be delivered, thus blood in this example, catching in the delivery blades and leading to an erection of the delivery blades by way of the counter pressure of the fluid.

The constructional shape of the rotor may also differ from that which has been described above, by way of using collapsible or pivotable elements, in order to form a delivery blade surface. The pivotable parts may then usefully be folded onto the drive shaft in the compressed condition.

The struts 13a, 13b as well as the frame 13c of the pump housing are usefully tautened, but the frame 13c runs in the direction of the pump housing somewhat beyond the tautening and forms a run-in chamfer there, which serves for a simpler displacement of the rotor into the pump housing.

Figure 3:
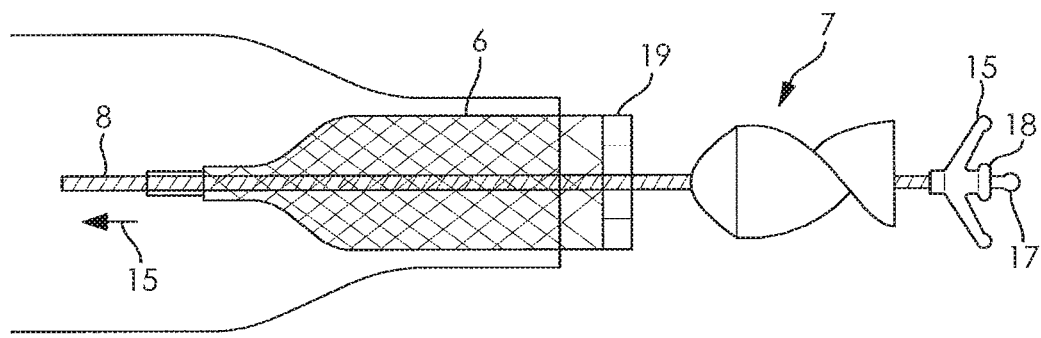

FIG. 3 shows a pump housing 6, a rotor 7 as well as a bearing arrangement 15, which are distributed distanced to one another axially on the drive shaft 8. This condition remains at least until the mentioned parts are brought within a body of a patient on location.

Thereafter, the drive shaft 8 which forms an actuation means, may be retracted in the direction of the arrow 15, in order to form a functioning construction unit of a fluid pump by way of a relative displacement of the rotor, pump housing and bearing arrangement.

On pulling-back the drive shaft 8, firstly the catch 17 abuts the hub 18 of the bearing arrangement 15. With a continued pulling-back of the shaft, the bearing arrangement is carried along and is pressed against the rotor 7. This is likewise carried along and, with the continued pulling back of the drive shaft 8, is pulled into the inside of the pump housing 6. Thereby, the rotor 7 moves so far into the pump housing, until it is completely covered by this.

The pump housing 6 at its open end carries a fixation ring 19, in which the struts of the bearing arrangement 15 may clamp.

Figure 4:
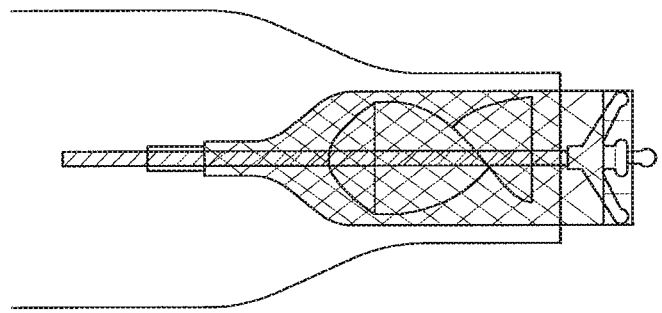
Figure 5:
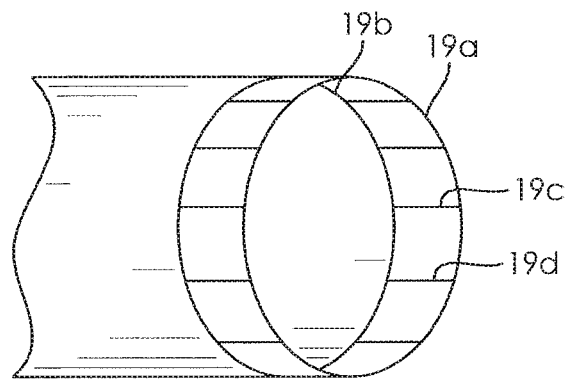

FIG. 4 shows the pump housing, the rotor and the bearing arrangement in an axially pushed-together form. The fixation ring 19 is described in more detail in FIG. 5. It consists of two individual rings 19a, 19b which are also coaxially positioned to one another and are connected by way of connection bars which are like ladder rungs. In each case, the ends of the struts 20, 21 of the bearing arrangement 15 have space between the connection bars 19c, 19d, so that after the introduction, the bearing arrangement is radially centred there as well as axially positioned with respect to the ring 19. The bearing arrangement is shown schematically in FIG. 6 and comprises a hub 18 and struts 20, 21. The struts 20, 21 are pivotably movably fastened on the hub 18 either by way of a joint or by way of their flexibility.

If the bearing arrangement is displaced with respect to the pump housing by way of pulling back the drive shaft, then the ends of the struts 20, 21 are applied elastically into the compartments between the bars 19c, 19d of the ring 19. There, the bearing arrangement braces automatically and centres the drive shaft mounted in its hub, with respect to the pump housing 6.

Figure 6:
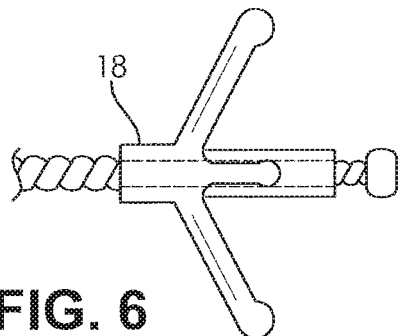
Figure 8:
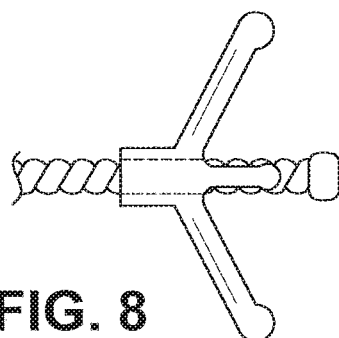

FIG. 6 shows a long bearing arrangement, with which in each case a significantly long hub piece is arranged in front of as well as axially behind the struts. The bearing arrangement may also be constructed in a shorter manner by way of a hub only being provided on one side of the struts, as is shown in FIG. 8.

Figure 7:
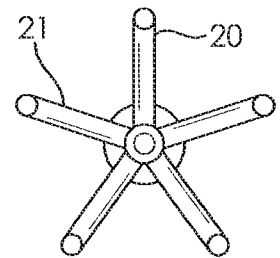

FIG. 7 shows a front view of the bearing arrangement of FIG. 6

Figure 9:

FIG. 9 shows the movement ability of the struts in the compressed condition.

On introducing the fluid pump device through a blood vessel into a human body, the struts 20, 21 firstly bear snugly on the hub body, as long as the bearing arrangement is still located within the vessel, and is then elastically expanded. This elasticity after the expansion and the axial contraction of the pump elements ensures that the bearing arrangement remains fixed in the ring 19 of the pump housing.

Figure 10:
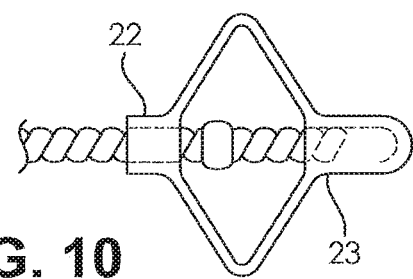

FIG. 10 shows a further embodiment of the bearing arrangement with a double shaft mounting and specifically in the region of the bearing 22, 23. The struts are formed and radially extended by way of two hub parts 22, 23 of the bearing arrangement approaching one another by way of axially pulling on the drive shaft. The struts on approaching the two hub parts are folded open on one another in a bead-like manner and extend radially away from the drive shaft. With an adequate expansion, these struts may also brace themselves in the ring 19.

Figure 11:
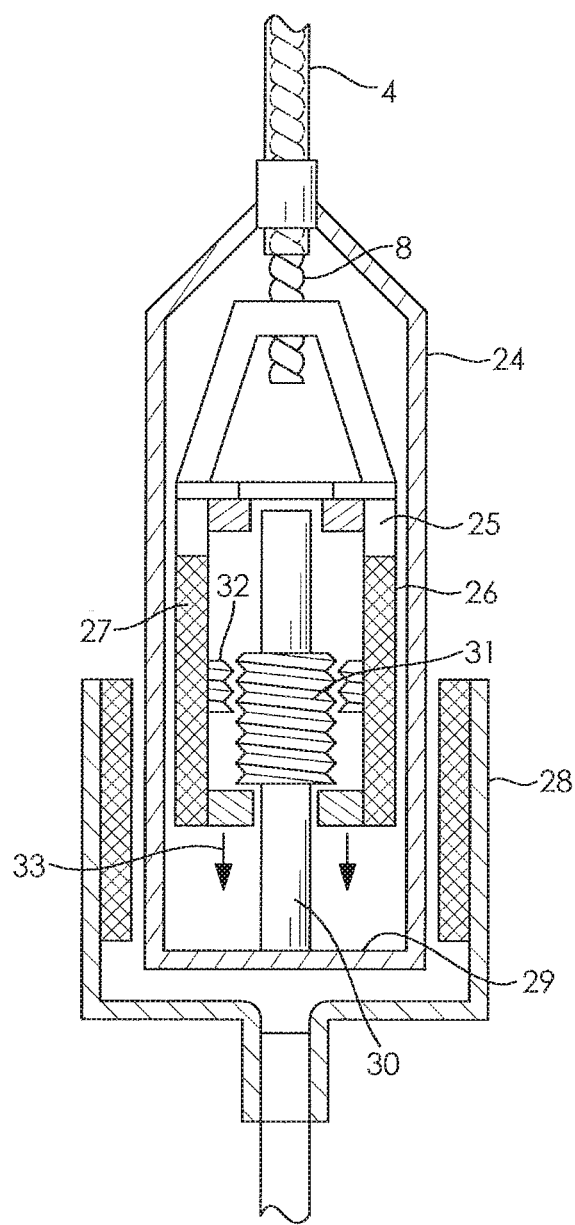

FIG. 11 shows the proximal end of the shaft 8 and its coupling to a drive, which is to permit an axial displacement ability of the drive shaft by 10 to 14 mm, in order after the introduction of the individual elements of the fluid pump to the application location, to be able to pull hack the bearing arrangement and the rotor into the pump housing by way of pulling back the drive shaft.

FIG. 11 in this context represents a gas-tight coupling of the catheter 4, which forms the sleeve for the shaft 8, onto a fluid-tight housing 24. A drive body 25 is located in the housing 24 and has magnet elements 26, 27 on its periphery, which on the cover side may be driven in a changing magnetic field incorporated outside the housing 24. A drive movement is transmitted by way of this in a simple manner via the fluid-tight wall of the housing 24. For example, a second drive body 28 with permanent magnets or electric magnets may rotate outside the housing 24, or windings may be arranged there, which produce a rotating field.

A bolt 30 is fastened on the base 29 of the housing 24 and carries a thread 31 which is stationary in the axial direction.

The rotor 25 carries a ring 32 with an inner thread which runs on the thread 31.

With a rotation of the drive body 25 in the operating direction, by way of the cooperation of inner and outer thread, the drive body 25 is moved in the direction of the arrow 33, by which means the drive shaft 8 is pulled back. The inner ring 32 after completion of the retraction movement of the shaft runs away from the thread 31, and as a result the drive body 25 may rotate axially in a stationary manner. The fluid pump is thus axially pushed together and set into operation.

Figure 12:
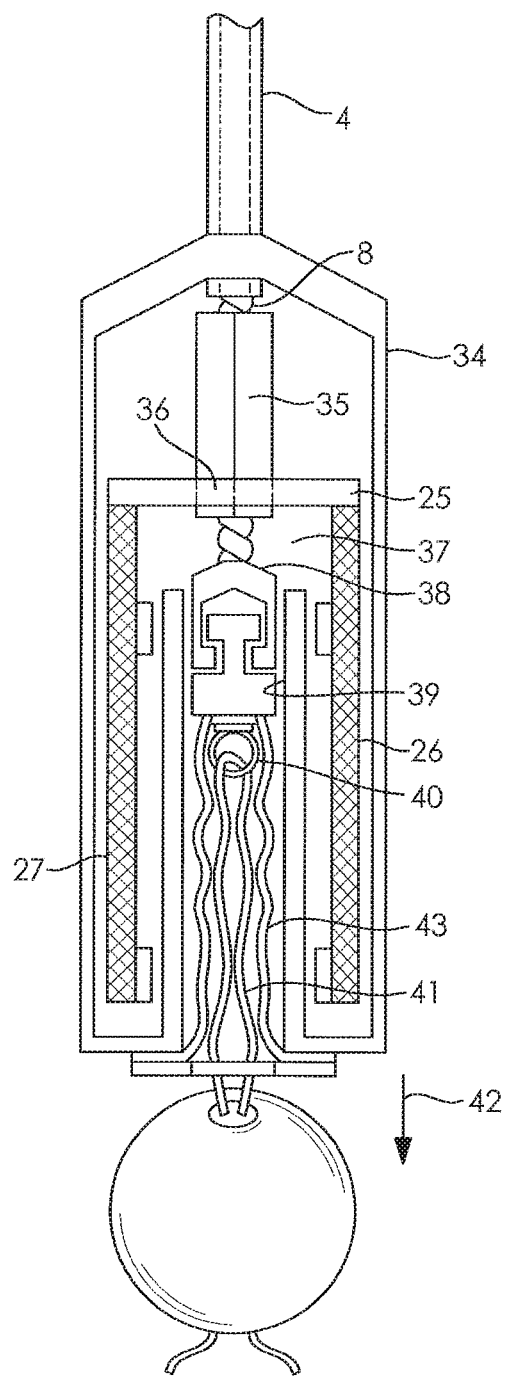

FIG. 12 shows another embodiment at the proximal end of the drive shaft 8. In the representation of FIG. 12, only the magnets 26, 27 of the drive body 25 which are located within a fluid tight housing 34 are represented. The drive body 25 may be mounted in the housing in an axially stationary manner and is driven in a rotational manner from the outside. It transmits the rotation movement onto a polygonal piece 35, which is guided in a complementarity shaped opening (lock) 36 in the drive body in a rotationally fixed manner, but axially displaceable manner with respect to this. For example the lock 36 and the polygonal piece 35 may be designed as a regular octagonal bolt, square bolt or hexagonal bolt.

The drive shaft 8 is connected in a rotationally fixed manner in its end region 37 to a bush 38. An armature 39 is rotatably received in the bush 38 with an undercut, and the armature does not rotate with the bush 38, but axially fixed this. The armature 39 is provided with a ring 40 through which a pull tape 41 is pulled. If the armature 39 is pulled back manually in the direction of the arrow 42 by way of the pull tape 41, then the armature pulls the bush 38, which may rotate with respect to the armature, in the direction of the arrow 42 a little out of the catheter 4, so that the necessary displacements may take place in the region of the fluid pump. The drive body 25 may be driven during this without upsetting the pulling movement.

The armature 39 may be fastened in a fluid-tight manner to the housing 34 by way of a bellows or a sealingly connected membrane 43, in order to ensure the sealedness of the housing 34.

Figure 13:
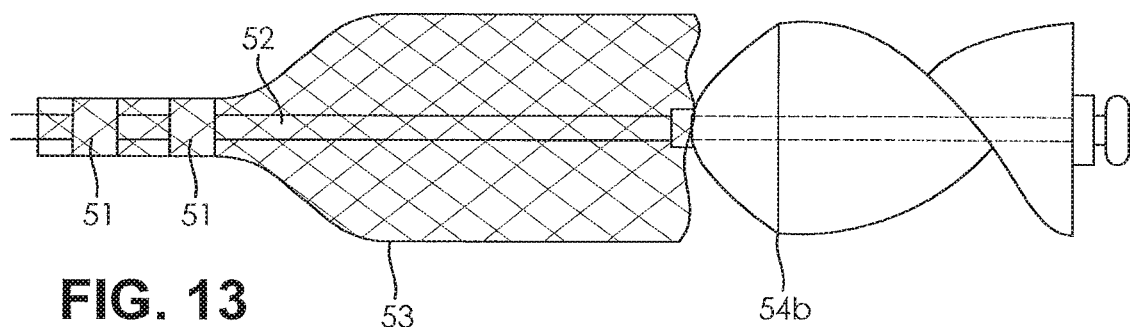

FIG. 13 shows a pump housing 53 which comprises a membrane which is spanned over a framework and ends in an open manner towards the distal end. The drive shaft 52 or its stiffened extension 52 is displaced distally to the pump housing, just as the rotor 54*b*. Two bearings 51, 51*a* are represented on the proximal side of the housing 53 and of the rotor, and are axially distant to one another and provide the drive shaft or its stiffened end with a particularly stable mounting, which also prevents a lateral swinging-open of the unmounted end on the other side of the bearings 51, 51*a*.

Instead of two separate bearings, one may also select an individual stable and preferably long bearing on the proximal side of the rotor. A simplified assembly and improved displacement ability with a greater running stability is realised by way of this.

Figure 14:
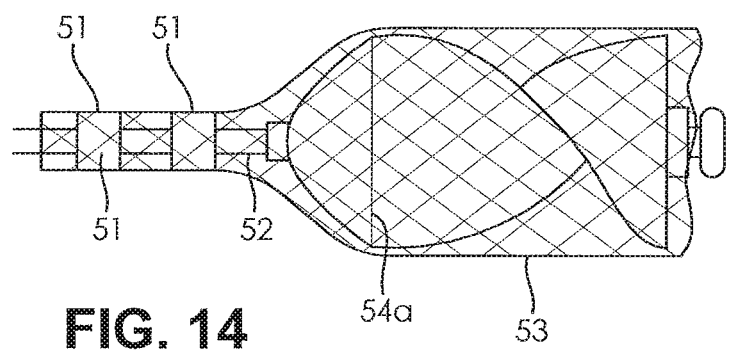

FIG. 14 shows the arrangement of FIG. 13 in the operating condition in which the shaft is pulled to the proximal end and the rotor 54*b* is pulled into the housing 53.

Figure 15:
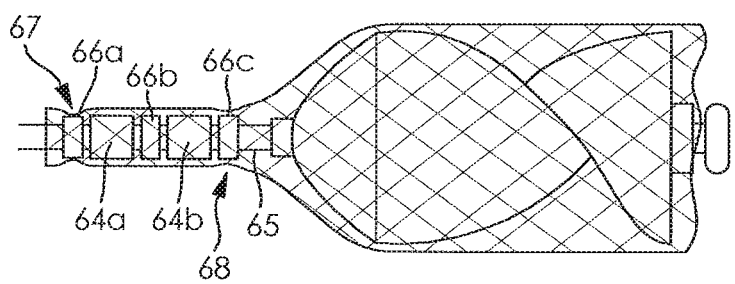

With longer flexible shafts, it makes sense to pull the rotor with locked bearings into the housing. In FIG. 15, the housing indentation 67 prevents the shaft with the locked bearings from being pulled too far inwards. The housing indentation 68 is thus not as deep as the housing indentation 67 and permits a pulling-in of the bearing combination. An axial displacement of the rotor combination to the outside is no longer possible by way of the snap-in. Bearings 64*a*+*b* are loose on the shaft 65. Locking sleeves 66*a-c* are connected to the shaft in a fixed manner.

Thus in all designs, an efficient manner of the drive with a displacement ability of the drive shaft is provided by way of the invention, wherein the displacement of the drive shaft, for completing the fluid pump after introduction to the place of operation, is used in an optimal manner by way of an axial relative displacement of the rotor, bearing arrangement and pump housing.

I claim:

1. An intravascular fluid pump device comprising:
 a pump housing having an open distal inflow end, the pump housing being expandable into an expanded state and compressible into a compressed state, wherein in the compressed state the pump housing is sized for percutaneous insertion into a vascular system of a patient;
 a radially compressible rotor disposed within the pump housing;
 a drive shaft having a proximal drive side end and a distal end, wherein the distal end is configured to transmit torque and rotate the radially compressible rotor relative to the pump housing;
 a distal bearing assembly located distal of the rotor, the distal bearing assembly comprising struts and a hub, the struts extending from the hub, wherein the struts brace between the hub and the pump housing.

2. The fluid pump device according to claim 1, wherein the struts do not rotate relative to the pump housing.

3. The fluid pump device according to claim 1, wherein in the compressed state, the struts are compressed such that they extend parallel to the drive shaft.

4. The fluid pump device according to claim 1, wherein the struts are configured to self-expand in the expanded state when the pump housing expands.

5. The fluid pump device according to claim 1, wherein the struts in a braced position form an inflow cage at the distal end of the fluid pump.

6. The fluid pump device according to claim 1, wherein the struts are pivotable and movably fastened on the hub.

7. The fluid pump device according to claim 6, wherein the struts are pivotable and movably fastened on the hub either by way of a joint or by way of their flexibility.

8. The fluid pump device according to claim 7, comprising a catheter having a distal portion coupled to the pump housing, wherein the drive shaft extends through the catheter.

9. The fluid pump device according to claim 1, wherein the drive-side end of the drive shaft is connected to a drive body.

10. The fluid pump device according to claim 9, wherein the drive body is an external motor.

11. The fluid pump device according to claim 9, wherein the drive body is an implantable motor, and an electrical lead is configured to be disposed within the patient and receive power from an electrical source located outside the patient.

12. The fluid pump device according to claim 11, wherein the drive body is arranged in a sealed housing, wherein the sealed housing is magnetically rotationally drivable from outside the housing.

13. The fluid pump device according to claim 8, wherein the pump housing is configured to self-expand into the expanded state.

14. The fluid pump device according to claim 13, wherein the catheter is configured for draining or filling hollow organs or spaces within a patient's body.

15. The fluid pump device of claim 14, wherein the fluid pump device is configured to be positioned in vasculature of a patient.

16. The fluid pump device of claim 15, wherein the fluid pump device is configured to be positioned in the left ventricle of the patient.

* * * * *

UNITED STATES PATENT AND TRADEMARK OFFICE
CERTIFICATE OF CORRECTION

PATENT NO. : 10,835,653 B2  
APPLICATION NO. : 16/369503  
DATED : November 17, 2020  
INVENTOR(S) : Reiner Liebing Page 1 of 1

It is certified that error appears in the above-identified patent and that said Letters Patent is hereby corrected as shown below:

On the Title Page

Column 1, (73):  
Now reads: "ENTWICKLUNGSESELLSCHAFT"; should read -- ENTWICKLUNGSGESELLSCHAFT --

In the Specification

Column 4, Line 7:  
Now reads: "beating"; should read -- bearing --

Column 7, Line 55:  
Now reads: "FIG. 6"; should read -- FIG. 6. --

Column 8, Line 12:  
Now reads: "hack"; should read -- back --

Signed and Sealed this  
First Day of March, 2022

Drew Hirshfeld  
*Performing the Functions and Duties of the*  
*Under Secretary of Commerce for Intellectual Property and*  
*Director of the United States Patent and Trademark Office*